(12) United States Patent
Ternamian

(10) Patent No.: US 6,638,265 B1
(45) Date of Patent: Oct. 28, 2003

(54) LAPAROSCOPY CANNULA ADAPTER AND ASSEMBLY

(75) Inventor: Artin Ternamian, Toronto (CA)

(73) Assignee: Artin M. Ternamian, Toronto (CA)

( * ) Notice: Subject to any disclaimer, the term of this patent is extended or adjusted under 35 U.S.C. 154(b) by 260 days.

(21) Appl. No.: 09/590,223

(22) Filed: Jun. 8, 2000

(51) Int. Cl.[7] ............................................ A61M 25/00
(52) U.S. Cl. ...................................................... 604/523
(58) Field of Search ................................ 604/523, 533, 604/264, 93.01

(56) References Cited

U.S. PATENT DOCUMENTS

| | | | | |
|---|---|---|---|---|
| 4,670,008 A | * | 6/1987 | Von Albertini | 604/165.01 |
| 4,997,419 A | * | 3/1991 | Lakatos et al. | 604/164.11 |
| 5,226,890 A | * | 7/1993 | Ianniruberto et al. | 604/164.04 |
| 5,248,298 A | * | 9/1993 | Bedi et al. | 604/264 |
| 5,573,518 A | * | 11/1996 | Haaga | 604/265 |
| 5,755,673 A | * | 5/1998 | Kinsey | 600/577 |
| 5,755,697 A | * | 5/1998 | Jones et al. | 604/174 |
| 5,800,451 A | * | 9/1998 | Buess et al. | 604/167.03 |
| 6,165,184 A | * | 12/2000 | Verdura et al. | 606/148 |
| 6,168,607 B1 | * | 1/2001 | Wattiez et al. | 606/185 |
| 6,217,568 B1 | * | 4/2001 | Jepson et al. | 604/167.02 |
| 6,247,592 B1 | * | 6/2001 | Racicot et al. | 206/366 |

\* cited by examiner

*Primary Examiner*—Daniel Robinson
(74) *Attorney, Agent, or Firm*—Baker Botts L.L.P.

(57) ABSTRACT

An adapter for use on an external surface of a laparoscopy cannula and a laparoscopy cannula assembly are disclosed wherein the adapter body has an inner surface for grasping the external surface of the cannula and has an outer surface for aiding in radial spreading of a body entrance and snugly engaging body tissue. The outer surface of the adapter body may be threaded or grooved and the inner surface of the adapter body coapts with the external surface of the cannula. An adapter fabricated in whole or in part from an elastomeric material that assists in snugly engaging the external surface of a cannula is also disclosed. Further, a method for aiding in the radial spreading of a body entrance opening during laparoscopy, and a method of maintaining the position of a cannula during laparoscopy is disclosed.

12 Claims, 7 Drawing Sheets

LAPAROSCOPY CANNULA ADAPTER AND ASSEMBLY

BACKGROUND OF THE INVENTION

This invention relates generally to instruments designed for accessing body cavities. More specifically, this invention relates to an adapter for a laparoscopy cannula and assembly.

Cannula assemblies traditionally have been used in laparoscopic surgery for several decades. In laparoscopy, a small incision is required to access an area where a wide range of surgical procedures can be performed with minimal traumna to the tissues. Until the invention described in this inventor's prior U.S. Pat. No. 5,478,329 and its division, U.S. Pat. No. 5,630,805, the disclosures of which are incorporated herein by reference, a surgeon would use a trocar assembly to gain access to the peritoneal cavity during a laparoscopic procedure. The trocar assembly included a trocar (also called an obturator) and a cannula, a tube through which the trocar is guided. Because the cannula end is blunt, in order to access the peritoneal cavity, the trocar would be used to pierce the layers of the anterior abdominal wall.

One such prior art trocar assembly is disclosed in U.S. Pat. No. 5,226,890. This trocar assembly includes a tissue engaging member, a guide tube member, and a collet for locking the tubular guide member to the externally smooth cannula. The conical tissue engager is helically threaded on its external surface so that it can be rotated into an incision to engage the tissue. Once the tissue engager is positioned, the trocar cannula is inserted into the bore of the tissue engager and is locked into place using the collet.

The principal disadvantage of using such a trocar assembly is that significant initial axial force is required to insert the trocar blindly through the layers of the anterior abdominal wall, transecting tissue along the way into the body cavity and increasing the possibility of the trocar being inadvertently inserted further into the abdominal cavity than is necessary or desirable, which could result in injury to major blood vessels or to other visceral organs.

The method and apparatus disclosed in U.S. Pat. Nos. 5,478,329 and 5,630,805 obviate such disadvantages. In a non-limiting embodiment, these patents disclose a trocarless cannula and a visual method for accessing a body cavity using such a trocarless cannula. Rather than the blunt-ended cannula of the then-prior art, the distal end of the trocarless cannula has a tip construction which incrementally and sequentially parts different tissue layers radially under vision along the port tract. The outer surface of the trocarless cannula includes a screw thread or groove which allows the cannula, after insertion via a small incision, to enter the body cavity, while maintaining a seal between the cannula body and the incision.

SUMMARY OF THE INVENTION

Therefore, a need has arisen for an improved trocarless cannula assembly which is able to better stabilize and hold the cannula in place. Such an improved trocarless cannula assembly should also improve and maintain an airtight seal between the cannula and the port site. And, as an added benefit, such an improved trocarless cannula assembly should also be able to steadily increase the size of the principal port into the body without transecting the tissues at port site, especially when a large surgical specimen needs to be removed.

To meet this need, the present invention provides an adapter for use on an external surface of a laparoscopy cannula, wherein the adapter, having a proximal end and a distal end, comprises a generally tubular body having an outer surface for radial spreading of a body entrance opening and snugly engaging body tissue, and an inner surface for grasping the internal surface of the cannula. The present invention further provides an adapter comprising a generally tubular body having a proximal end, a distal end, and an inner surface forming a lumen within the body extending throughout its entire length, an outer surface, and means on the inner surface of the adapter body for grasping the external surface of the cannula, wherein the proximal end of the adapter body has a larger diameter than the distal end of the adapter body to aid in radial spreading of a body entrance opening.

The adapter further comprises a means on the outer surface of the adapter body for snugly engaging body tissue. For example, a means of doing this is for the adapter body to have one or more helical thread(s) or groove(s) of a fixed or variable pitch on the outer surface. The adapter body preferably is tapered in its diameter from the proximal end to the distal end. One embodiment of this taper is for the adapter body to be substantially conically shaped. It is also preferable for the outside diameter at the distal end to approach the outside diameter of the cannula. The adapter may optionally include a suture holding mechanism to secure a suture to the patient's body. The suture holding mechanism may be a notch in the adapter body, or an arm or rod attached to the adapter body. An adapter in accordance with the present invention can be part of an open or closed laparoscopy cannula assembly.

A variety of means on the inner surface of the adapter body for grasping the external surface of the cannula are contemplated that coapt with the external surface of the cannula. The external surface of the cannula may be smooth, threaded or grooved and fabricated from single or multiple use materials. The inventive adapter may be fabricated from traditional single or multiple use materials, or may be fabricated in whole or in part from an elastomeric material that snugly engages the external surface of the cannula. The internal surface of the inventive adapter may be smooth, threaded or grooved.

For adapters fabricated of traditional single or multiple use materials, the means on the inner surface of the adapter body for grasping the external surface of the cannula would depend upon the external configuration of the cannula. For example, a cannula having an external helical thread would require an adapter body having a coapting inner helical groove, and a cannula having an external helical groove would require an adapter body having an inner helical thread.

For adapters fabricated in whole or in part from an elastomeric material that snugly engages the external surface of a cannula in accordance with the present invention, the means for grasping on the inner surface of the adapter body may be configured to coapt with the external surface of the cannula, or may be designed to coapt with any configuration of the external surface of the cannula. For example, an adapter having an elastomeric inner surface may be designed having a helical thread that coapts with an external helical groove of the cannula and an adapter having an elastomeric inner surface may be designed having a helical groove that coapts with an external helical thread of the cannula. Further, the adapter having an elastomeric inner surface may be designed with a smooth inner surface that is capable of firmly grasping the external surface of a smooth, threaded or grooved cannula because of the elasticity of the deformable elastomeric material.

Alternatively, the external surface of the laparoscopy cannula may comprise an elastomeric material, wherein the elastomeric material has a helical thread or groove that is designed to coapt with a helical groove or thread of a laparoscopy cannula adapter. Further, the elastomeric outer surface of the cannula may be designed with a smooth outer surface that is capable of grasping a smooth, threaded or grooved internal surface of a laparoscopy cannula adapter.

The present invention further provides for a laparoscopy cannula adapter assembly comprising a laparoscopy cannula having an external surface and an adapter comprising a generally tubular body having an outer surface for aiding in radial spreading of a body entrance opening and snugly engaging body tissue, and an inner surface of said body for grasping the external surface of the cannula.

The cannula or adapter may be made entirely of the elastomeric material contemplated by the present invention or may be applied as a surface coating on the cannula or adapter, and may be threaded, grooved, smooth or may have protruding nubs of elastomer.

The invention is further directed to a method for aiding in the radial spreading of a body entrance opening during laparoscopy to facilitate removal of large surgical specimen without having to transect tissues along the port tract, the method comprising accessing the peritoneal cavity through the body entrance opening using a cannula and winding an adapter that grasps the external surface of the cannula as it winds down the cannula until the adapter lodges into the body entrance opening, wherein the body entrance opening is radially spread by the external surface of the adapter body.

Also in accordance with the present invention is a method of maintaining the position of a cannula during laparoscopy, the method comprising accessing the peritoneal cavity through the body entrance opening using a cannula, positioning the cannula at a desired depth inside the body entrance, winding an adapter that grasps the external surface of the cannula as it winds down the cannula until the adapter body lodges into the body entrance opening, and radially spreading the body tissue at the body entrance, wherein the engagement between the body tissue, the adapter, and the cannula maintains the position of the cannula during laparoscopy.

BRIEF DESCRIPTION OF THE DRAWINGS

For a more complete understanding of the present invention and the advantages thereof, reference is now made to the following description taken in conjunction with the accompanying drawing, wherein like reference numerals represent like parts.

DETAILED DESCRIPTION OF THE INVENTION

Figure 1:
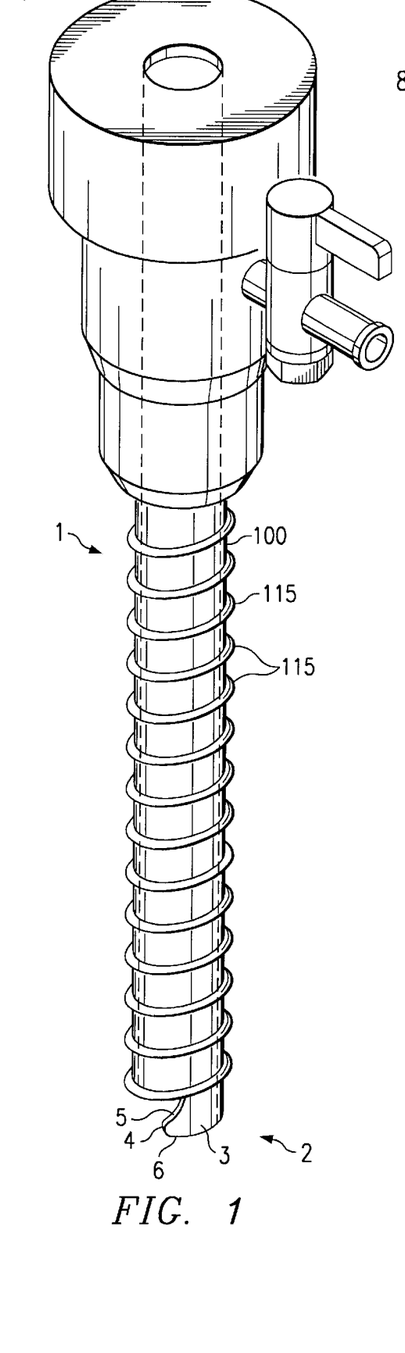
FIG. 1 is a perspective view of a cannula according to applicant's prior U.S. Pat. Nos. 5,478,329 and 5,630.805.

The applicant's prior patents disclose a trocarless cannula 1, shown in FIG. 1, and a visual method for accessing a body cavity using such a trocarless cannula. Rather than the blunt-ended cannula of the then-prior art, the blunt distal end 2 possesses means of radially parting tissue layers of the body wall. Penetrating means includes a distal end hook 3 with a sharp or blunt tip 4 and an upper margin 5 and a lower margin 6, each of which could also be either blunt or sharp or partially both. The outer surface of the illustrated trocarless cannula 100 includes a helical thread 115. A small skin incision is made and the underlying tissues down to the anterior fascia, sufficient in size to allow passage of the cannula. Then a smaller incision is made in the anterior fascia to allow the tip of the cannula to engage the anterior fascia. The cannula of FIG. 1 is then rotated clockwise and the different tissue layers are seen to sequentially part radially and are then lifted and transposed on to the outer thread. The tissues are incrementally pulled up on the rotating cannula under vision while maintaining a seal around the cannula body.

Figure 2A:
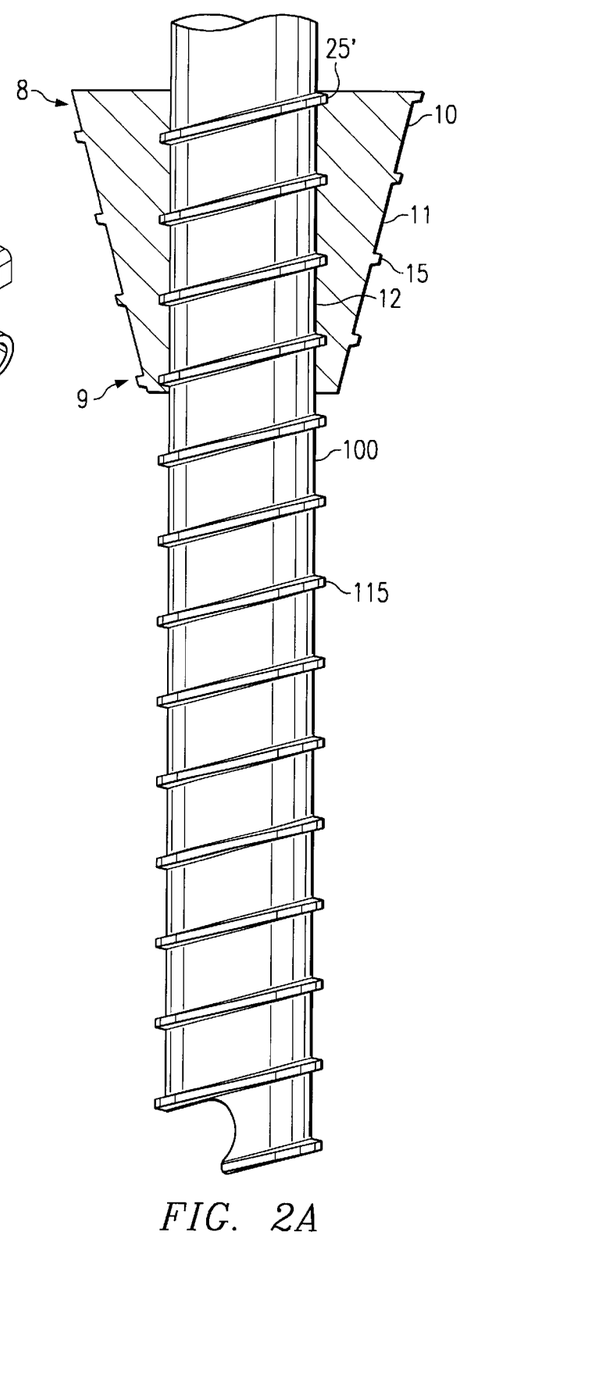
FIG. 2A is a side view of a portion of the cannula of FIG. 1 having an external helical thread and an adapter in accordance with the present invention, shown in cross-section, having an external helical thread and an internal helical groove that coapts with the cannula.

FIG. 2A illustrates a threaded trocarless cannula 100 of FIG. 1 and an improved adapter 10 designed to grasp the external surface of the laparoscopy cannula 100, wherein the adapter comprises a body having a proximal end 8, a distal end 9, an inner surface 12 forming a lumen within the body extending throughout its entire length, and an outer surface 11. The proximal end 8 of the adapter has a larger diameter than the distal end 9 to aid in the radial spreading of a body entrance opening. The inventive adapter further comprises a means on the inner surface for grasping the external surface of the cannula. In FIG. A, the means is illustrated as a groove 25' that coapts with thread 115 on cannula 100. The outer surface of the adapter 10 is provided with means for snugly engaging body tissue, illustrated in this embodiment as a helical thread 15.

Figure 2B:
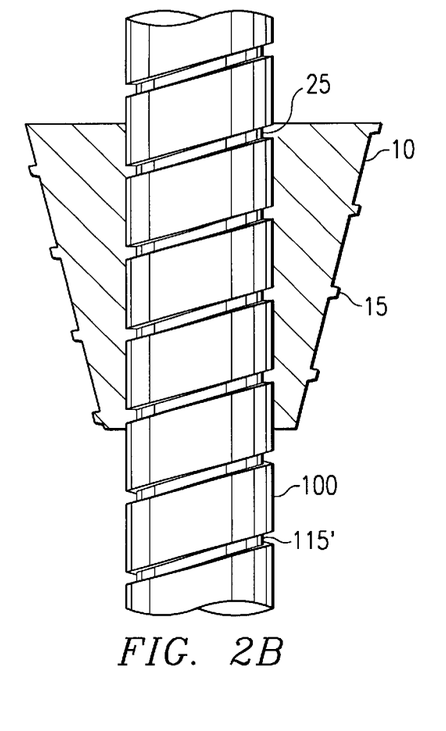
FIG. 2B is a side view of a portion of the cannula according to applicant's prior U.S. Pat. Nos. 5,478,329 and 5,630,805 having an external helical groove and another adapter in accordance with the present invention shown in cross-section having an external helical thread and an internal helical thread that coapts with the cannula.

FIG. 2B illustrates a grooved trocarless cannula 100 as described in applicant's two prior U.S. patents and an improved adapter 10 designed to grasp the external surface of the laparoscopy cannula 100, wherein the means on the inner surface of the adapter for grasping the external surface of the cannula 100 is illustrated as a thread 25 that coapts with the groove 115' on cannula 100. The external surface of the adapter 10 comprises a helical thread 15.

Figure 2C:
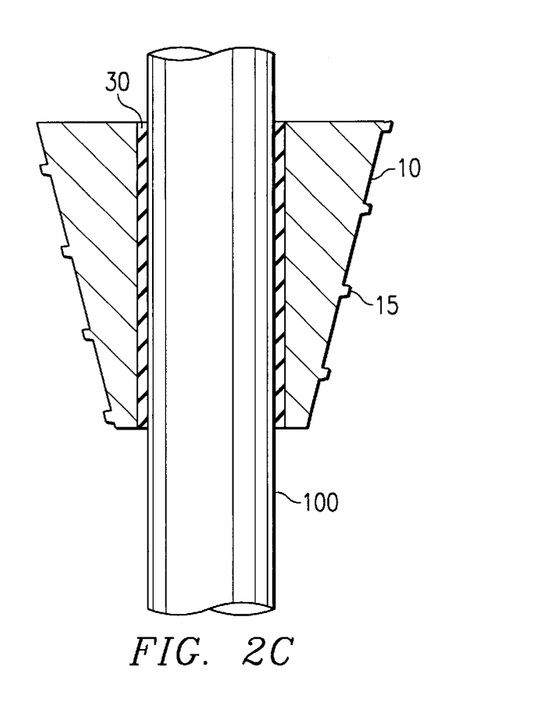
FIG. 2C is a side view of a portion of a prior art cannula having a smooth external surface and another adapter in accordance with the present invention shown in cross-section having an external helical thread and a smooth elastomeric interior surface.

FIG. 2C illustrates another improved adapter 10 designed to grasp the external surface of a smooth, grooved or threaded cannula 100. The cannula 100 illustrated in FIG. 2C is a smooth cannula, known in the art. The inventive adapter 10 comprises an elastomeric material 30 along the inner surface that grasps the external surface of the cannula 100. The outer surface of the adapter 10 comprises a helical thread 15.

Adapter 10 can be made from any of traditional single or multiple use materials including but not limited to TEFLON®, natural rubber, synthetic rubber, plastics and thermoplastics, or metals including but not limited to aluminum and stainless steel. The materials used may be rigid or flexible, and the entire adapter may be fully rigid or fully flexible or may comprise a rigid portion and a flexible portion. In addition, adapter 10 may be fully disposable or fully reusable or may comprise a disposable portion and a reusable portion. According to the invention, the adapter may be made in whole or in part from an elastomeric material. The elastomeric material of the present invention includes, and is not limited to, one or more of the following materials: natural rubber, synthetic rubber, plastics and thermoplastics having a suitable elasticity.

As disclosed in applicant's prior patents, cannula 100 may be made from any of traditional single or multiple use materials used in the field including but not limited to TEFLON®, natural rubber, synthetic rubber, plastics and thermoplastics, or metals including but not limited to aluminum and stainless steel. The materials used may be rigid or flexible, and the entire cannula may be fully rigid or fully flexible or may comprise a rigid portion and a flexible portion. In addition, cannula 100 may be fully disposable or fully reusable or may comprise a disposable portion and a reusable portion. According to the invention, the cannula may be made in whole or part from an elastomeric material that engages an adapter. In one particular embodiment, a laparoscopy cannula of this invention comprises a distal end, a proximal end, and an outer surface wherein the outer surface comprises an elastomeric material. The elastomeric material may be present throughout the cannula or may be a coating applied to the outer surface of the cannula. The elastomeric material of the cannula may be the same as or different from the elastomeric material of the adapter.

Figure 3A:
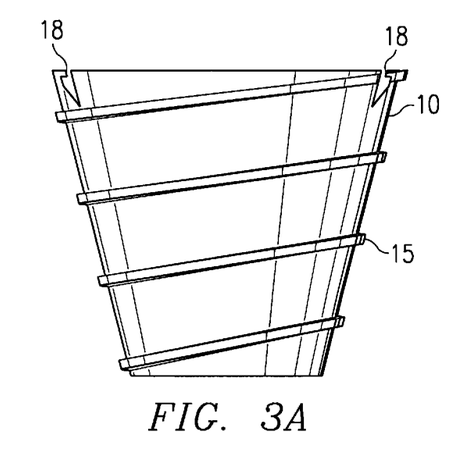
FIGS. 3A, 3C and 3E are a side view, top view and bottom view, respectively, of another adapter in accordance with the present invention having an external helical thread. an internal helical groove. and a notch in the adapter body as a suture holding mechanism.

The adapter 10 as illustrated herein is generally conical in shape. However, the contour of the outer surface of the adapter may have a variety of shapes to aid in the radial spreading of body tissue. The surfaces may be designed as being a generally conical, wherein the outside diameter of the adapter generally tapers from the proximal end to the distal end. The taper may be convex, concave or straight. It is preferable for the outside diameter at the distal end to approach the outside diameter of the cannula. In addition to the generally conical shape of the adapter, the present invention further provides additional means for snugly engaging body tissue on the outer surface of the adapter. Examples of means for snugly engaging body tissue include one or more helical thread(s) and/or groove(s) on the outer surface of the adapter body. FIG. 3A shows an example of an external helical thread 15 and FIG. 3B shows an example of an external helical groove 15'.

Examples of means for grasping the inner surface of the adaptor include (1) groove(s) designed to coapt with screw threads on the external surface of the cannula (e.g., FIG. 2A), (2) threads designed to coapt with groove(s) on the external surface of the cannula (e.g., FIG. 2B), (3) a moldable elastomeric material on the internal surface of the adaptor designed to coapt with either thread(s), groove(s), or a smooth external surface of the cannula (e.g., FIGS. 2C and 4A), (4) groove(s) or thread(s) of a moldable elastomeric material designed to coapt with the external surface of the cannula (e.g., FIGS. 4B and 4C), and (5) protruding nubs of elastomeric material (e.g., FIGS. 4E, 4F, 5A and 5B). In FIGS. 2A, 2B, 3G, 4B, 4C, 7A and 7B, the pitch of the helical thread or groove on the internal surface of the adapter is designed to coapt with the pitch of the groove or thread on the external surface of the cannula. For example, FIGS. 2A and 2B show a groove 25' and thread 25, respectively, on the inner surface of the adapter 10 having a pitch substantially the same as that of cannula thread 115 and groove 115', respectively. The pitch is the distance between one point on a thread or groove and the corresponding point on the next thread or groove. The pitch of external adapter helical thread 15 or groove 15' may be the same, greater than or less than the pitch of the thread 115 or groove 115' of the cannula.

Figure 3B:
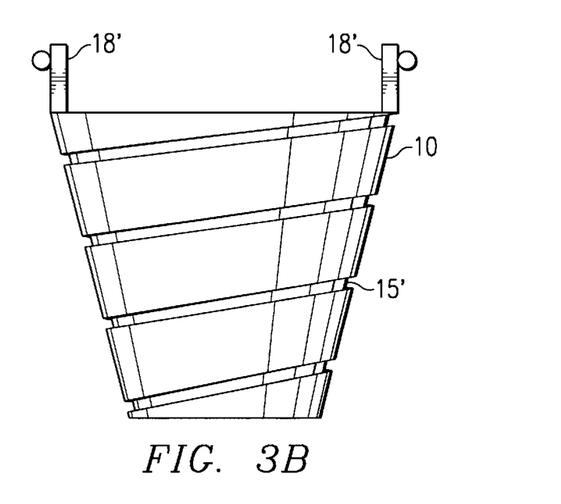
FIGS. 3B, 3D and 3F are a side view, top view and bottom view, respectively, of another adapter in accordance with the present invention having an external helical groove, an internal helical thread, and a rod attached to the adapter body as a suture holding mechanism.
Figure 3C:
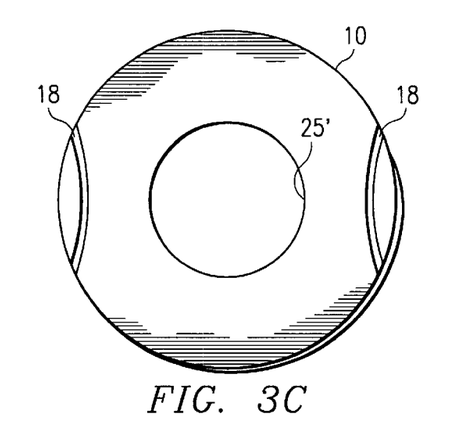
Figure 3D:
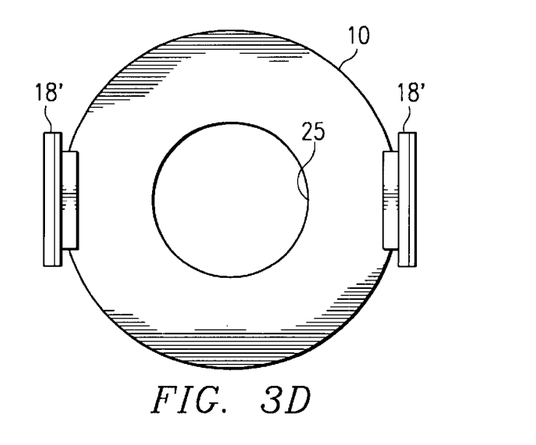
Figure 3E:
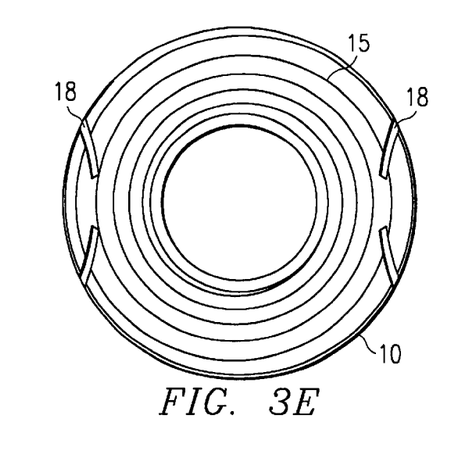
Figure 3F:
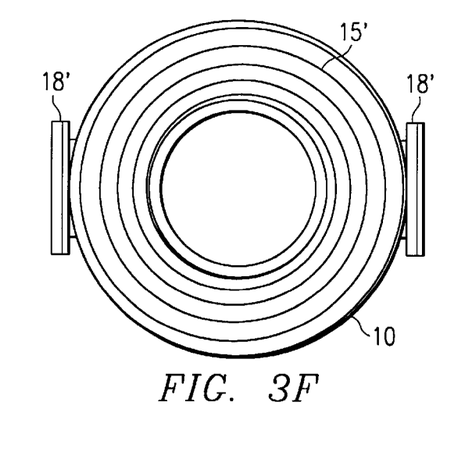
Figure 3G:
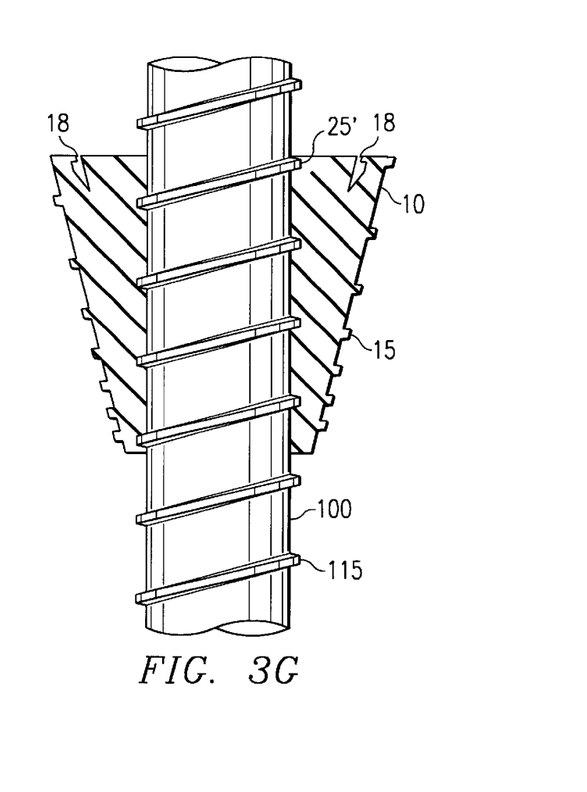
FIG. 3G is a cross-sectional view of an adapter, wherein the adapter is made of an elastomeric material throughout the body of the adapter and wherein the adapter body has a variable pitch on the outer surface.
Figure 4A:
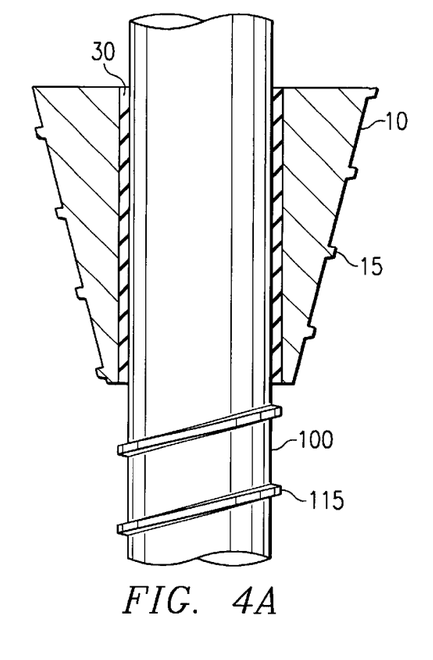
FIGS. 4A–4E are cross-sectional views of additional embodiments of adapters in accordance with the present invention having an elastomer on the inner surface of the adapter.
Figure 4B:
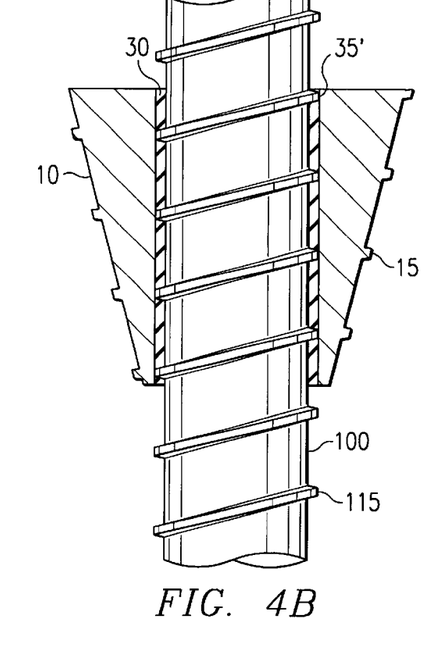
Figure 4C:
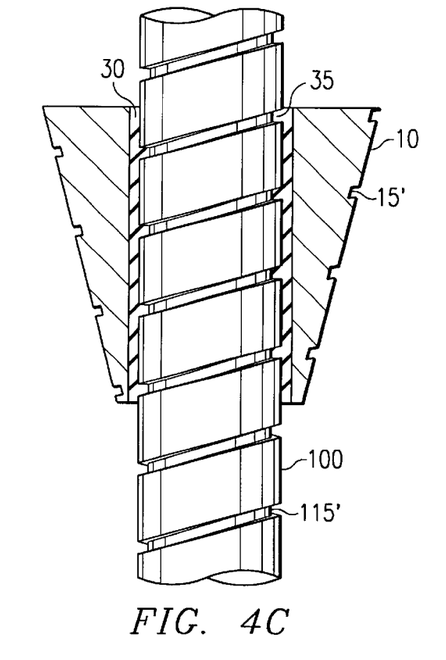
Figure 4D:
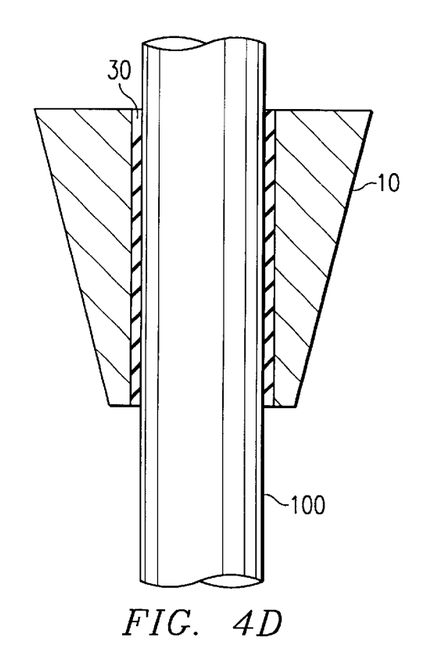

FIGS. 3A–3G show views of additional embodiments of inventive adapter 10. FIGS. 3A, 3C and 3E are a side view, top view and bottom view, respectively, of adapter 10 having an external helical thread 15, an internal groove 25' and an example of a suture holding mechanism 18, shown as a notch 18 in the adapter body, which may optionally be used to stabilize the adapter, and thereby the cannula, to an external point. For example, a suture may be secured between the notch 18 and the patient's body. FIGS. 3B, 3D and 3F are a side view, top view and bottom view, respectively, of adapter 10 having an external helical groove 15', and internal helical groove 25', and another example of a suture holding mechanism 18, shown as a rod 18' attached to the adapter body, which may optionally be used to secure a suture between the rod 18' and the patient's body. Any conventional suture holding mechanism may be substituted for the notch 18 and rod 18' as shown in FIGS. 3A–F, including an embodiment wherein the suture holding mechanism is mounted to a collar that is mounted to the proximal end of the adapter. FIG. 3G is a cross-section of adapter 10 showing outside helical thread 15 having a variable pitch and inside groove 25' according to FIG. 3A wherein the adapter 10 is made of an elastomeric material through the body of the adapter 10.

Figure 4E:
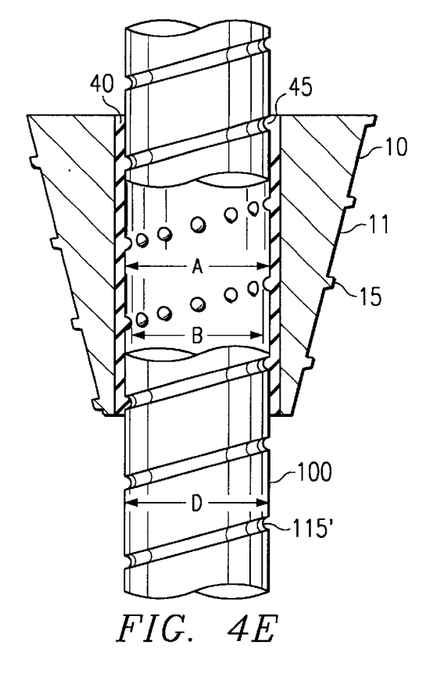
Figure 4F:
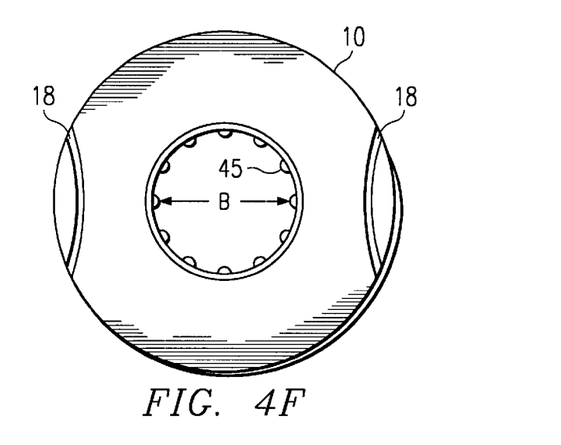
FIG. 4F is a top view of the inventive adapter of FIG. 4E further containing optional notches in the adapter body as a suture holding mechanism.
Figure 5A:
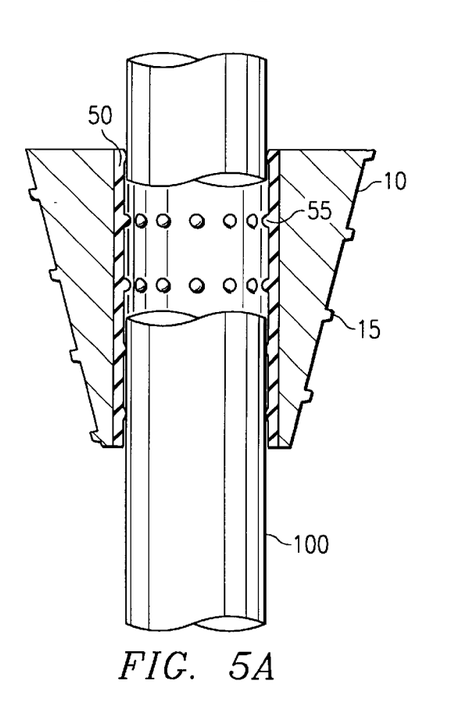
FIGS. 5A–5B are a cross-sectional and top view, respectively, of additional embodiments of an adapter in accordance with the present invention having protruding nubs or protuberances of elastomer on the inner surface of the adapter with (FIG. 5B) and without (FIG. 5A) an optional surface holding mechanism.
Figure 5B:
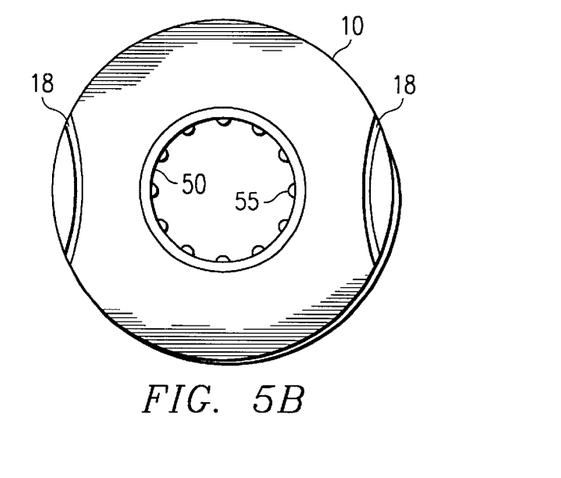
Figure 6A:
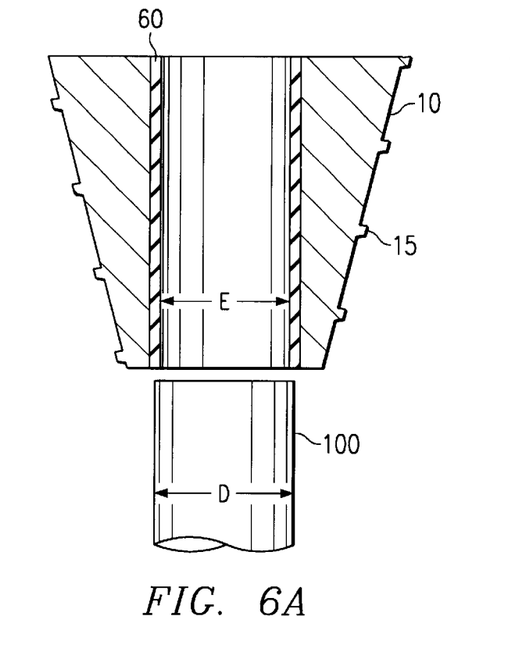
FIGS. 6A–6C are cross-sectional views of additional embodiments of an adapter in accordance with the present invention having an elastomeric inner surface and a threaded, grooved and smooth outer surface, respectively.
Figure 6B:
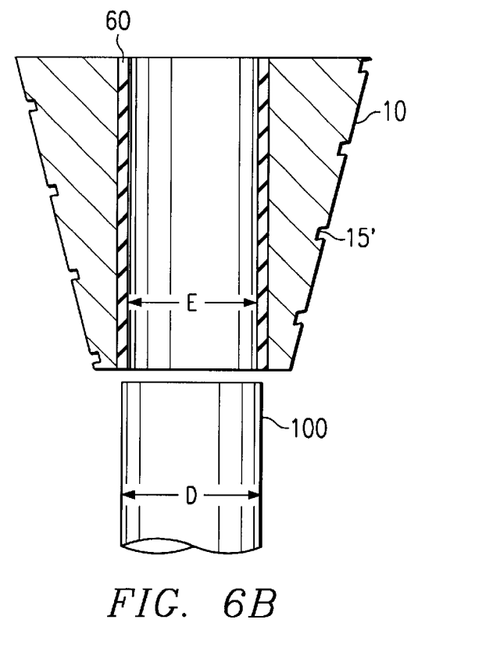
Figure 6C:
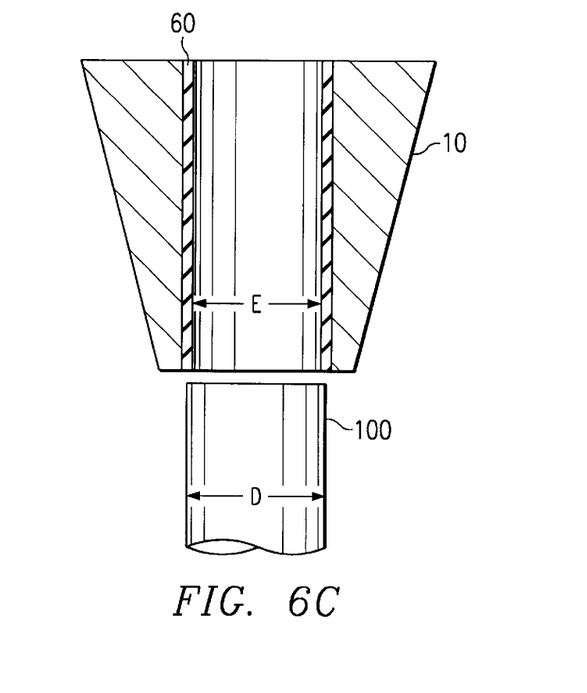

Additional alternative embodiments of adapter 10 are pictured in FIGS. 4, 5, and 6 wherein the internal surface of the adapter comprises a moldable elastomeric material that may line the internal surface of the adapter 30 or that may be contained throughout the adapter 10. For example, adapter 10 may have (1) a smooth elastomeric lining 30 (e.g., FIGS. 4A, 4D and 6A) designed to coapt with a smooth, threaded or grooved cannula, (2) a preformed groove 35' to coapt with a threaded cannula (e.g., FIG. 4B), or (3) a preformed thread 35 (e.g., FIG. 4C) to coapt with a grooved cannula. In FIG. 4A, as adapter 10 is wound down around a smooth and then threaded cannula, grooves are formed in inside lining 30, creating an airtight seal and a rigid connection between cannula 100 and adapter 10. Thus, when adapter 10 is fully wound down into the body entrance opening, adapter 10 snugly grasps cannula 100.

In alternative embodiments shown in FIGS. 4E, 4F, 5A, and 5B, the adapter 10 may be provided with protruding nubs which may be randomly or systematically placed along the interior surface of the adapter to engage the cannula. FIGS. 4E and 4F illustrate in cross-section and in top view, respectively, an adapter according to the present invention wherein the internal surface of the adapter 40 possesses protruding nubs in the pattern of a thread 45. Another contemplated pattern of nubs would form rings (e.g., FIG. 5A). The diameter A of inside lining 40 is just slightly larger than the diameter D of cannula 100, while the diameter B measured between the threads is just slightly smaller than the diameter D of cannula 100. Thus, a tight seal can be formed between adapter 10 and cannula 100 as adapter 10 is wound down cannula 100. FIG. 5B illustrates an additional embodiment wherein the protruding nubs are randomly placed along the inner surface of the adapter. In this figure, inner surface 50 possesses protruding nubs 55 which may be randomly placed along inside lining 50.

In further embodiments of the invention illustrated in FIGS. 6A–6C, the inner elastomeric lining 60 has a generally constant inside diameter E that is slightly smaller than the diameter D of cannula 100. Because the elastomeric lining 60 is compressible, adapter 10 can be wound down cannula 100. FIGS. 6B and 6C illustrate alternative embodiments of the adapter of FIG. 6A wherein the external surface of the adapter is grooved or smooth. In a further alternative embodiment, the elastomeric material in FIGS. 6A–6C is present throughout the adapter 10.

Figure 7A:
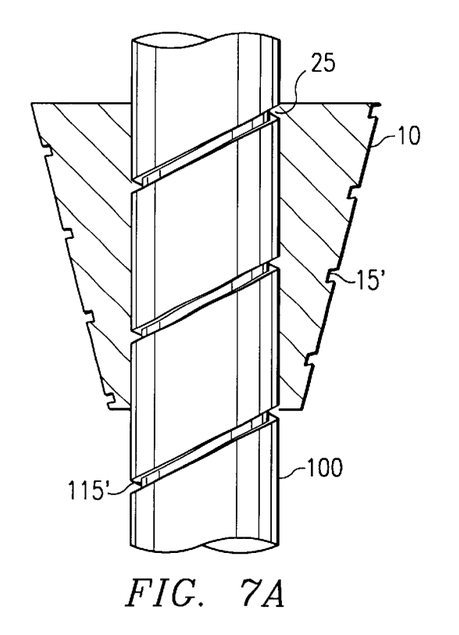
FIG. 7A is a cross-sectional view of another embodiment of an adapter in accordance with the present invention, wherein the pitch of the external groove of the adapter is approximately twice the pitch of the external groove of the cannula.
Figure 7B:
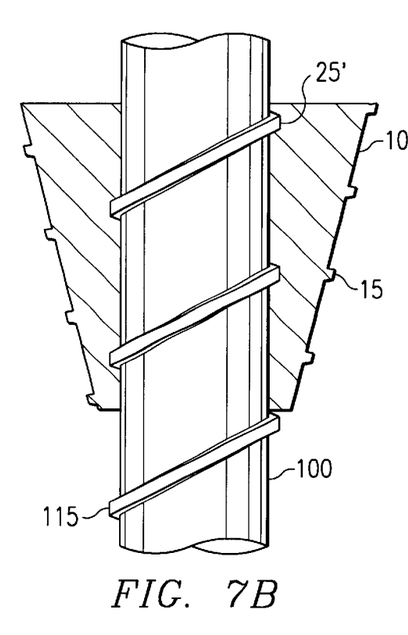
FIG. 7B is a cross-sectional view of another embodiment of an adapter of the present invention, wherein the pitch of the external thread of the cannula is approximately twice as great as the pitch of the external surface of the adapter.
Figure 7C:
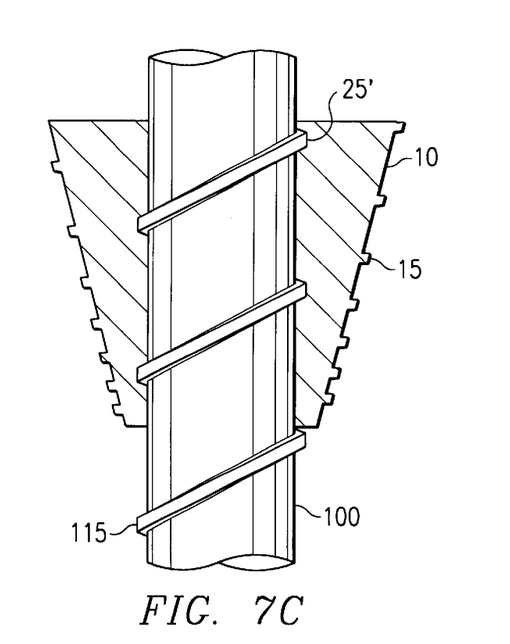
FIG. 7C is a cross-sectional view of another embodiment of an adapter of the present invention. wherein the pitch of the external thread of the adapter is variable.

In additional embodiments of the present invention shown in FIG. 7, the external adapter groove 15' or thread 15 may have a pitch that is the same, greater, or less than the pitch of the external thread 115 or groove 115' of the cannula. By varying the pitch, the practitioner may be able to evoke greater control over placement of the adapter into the patient's body by altering the number of rotations of the adapter required for the adapter to travel along the cannula. As shown in FIG. 7A, the pitch of the external groove 15' of the adapter is approximately half the pitch of the external groove 115' of the cannula. Illustrated in FIG. 7B is a cannula having an external thread 115 having a pitch that is approximately twice as great as the pitch of external adapter thread 15. FIG. 7C further illustrates an external adapter thread 15 having a variable pitch. Decreasing the pitch of the external adapter thread or groove with respect to the external surface groove or thread of the cannula allows the adapter to be wound down the cannula relative quickly. However, as adapter 10 is wound down cannula 100 and begins to engage the body tissue, the smaller external pitch of the adapter causes the rate of rotation of the adapter to slow down and thereby provides greater control of the radial spreading of the body tissue.

The present invention is further directed to a method for aiding in the radial spreading of a body entrance opening during laparoscopy. The method comprises accessing the peritoneal cavity through the body entrance using a cannula and winding an adapter that grasps the external surface of the cannula as it winds down the cannula until the adapter lodges into the body entrance opening, thereby radially spreading the body entrance opening by the external surface of the adapter. Once the cannula adapter assembly is removed, a substantial opening exists to facilitate the removal of large surgical specimen without having to transect tissues along the port tract and without cutting the specimen into pieces small enough to remove through the cannula.

The present invention is further directed to a method of maintaining the position of a cannula during laparoscopy. The method comprises accessing the peritoneal cavity through a body entrance opening using a cannula, positioning the cannula at a desired depth inside the body entrance, winding an adapter that grasp the external surface of the cannula as it winds down the cannula until the adapter lodges into the body entrance opening, and radially spreading the body tissue at the body entrance, wherein the engagement between the body tissue, the adapter, and the cannula maintains the position of the cannula during laparoscopy. The method further comprises applying a suture between the lodged adapter body and an external source, such as the body. By using a laparoscopy cannula adapter, described and illustrated herein, that grasps the external surface of the cannula, the adapter maintains the position of the cannula in relation to the body.

In summary, the present invention provides an improved cannula adapter that grasps the external surface of the cannula with the internal surface of the adapter After the cannula has penetrated the body cavity, the adapter can be brought down towards the distal end of the cannula so as to hug the port site tissues more intimately and to lodge within the entrance opening made by the cannula. The outside of the adapter engages the patient's body tissue and stabilizes the cannula adapter assembly with respect to the body. Because of the tapered, generally conical shape of the adapter, the adapter is able to radially spread the entrance opening without transecting tissues along the port tract. The adapter also seals the body entrance opening at the point of the incision and discourages gas leakage or loss through the port site during the surgery. In addition, it allows an atraumatic way of removing large surgical specimen through the primary port site without transecting tissue and without cutting the specimen inside the patient's body.

While several embodiments of the invention have been illustrated and described, other variations and alternate embodiments will occur to those skilled in the art. These variations and embodiments are still within the spirit and scope of this invention.

I claim:

1. An adapter for use on an external surface of a cannula for laparoscopy, the adapter having a proximal end and a distal end comprising a generally tubular body having an outer surface for aiding in radial spreading of a body entrance opening and snugly engaging body tissue, and an inner helical grasping surface for grasping the external surface of the cannula.

2. The adapter according to claim 1, wherein said outer surface comprises a thread.

3. The adapter according to claim 1, wherein said outer surface comprises a groove.

4. The adapter according to claim 1, wherein said inner surface comprises a thread.

5. The adapter according to claim 1, wherein said inner surface comprises a groove.

6. The adapter according to claim 1, wherein said inner surface comprises an elastomer.

7. The adapter according to claim 1, wherein said outer surface of said body comprises a thread or groove having a first pitch and the inner surface of said body comprising a thread or groove having a second pitch.

8. The adapter according to claim 7, wherein the first pitch is less than the second pitch.

9. The adapter according to claim 1, wherein said outside diameter of said body tapers from said proximal end to said distal end.

10. The adapter according to claim 9, wherein said body is substantially conically shaped.

11. The adapter according to claim 1, further comprising a suture holding mechanism.

12. The adapter according to claim 11, wherein said suture holding mechanism is selected from the group consisting of a notch in said body, an arm attached to said body and a rod attached to said body.

* * * * *